United States Patent [19]

McLoughlin et al.

[11] Patent Number: 4,956,386
[45] Date of Patent: Sep. 11, 1990

[54] PHARMACEUTICAL COMPOSITIONS AND PROCESS FOR THEIR PREPARATION

[75] Inventors: Christopher J. McLoughlin, Johannesburg, South Africa; Ross B. Himstedt, Kenmore, Australia

[73] Assignee: Gist-Brocades N.V., Delft, Netherlands

[21] Appl. No.: 756,555

[22] Filed: Jul. 17, 1985

Related U.S. Application Data

[63] Continuation of Ser. No. 143,797, Apr. 25, 1980, abandoned, which is a continuation of Ser. No. 592,636, Jul. 2, 1975, abandoned, which is a continuation-in-part of Ser. No. 543,862, Jan. 24, 1985, abandoned.

[51] Int. Cl.$^5$ .............................................. A61K 31/29
[52] U.S. Cl. .................................... 514/503; 424/617; 424/653
[58] Field of Search ....................... 424/166, 653, 617; 514/503

[56] References Cited

U.S. PATENT DOCUMENTS

3,920,972  11/1975  Beekman ............................ 424/157
4,042,685   8/1977  Smith ................................. 424/158

FOREIGN PATENT DOCUMENTS

1414121  9/1971  United Kingdom ................ 424/158

OTHER PUBLICATIONS

*S. A. Medical Journal*, vol. 42, Mar. 30, 1968, pp. 317–320.
Webster Seventh New Collegiate Dictionary ©1967, p. 163.
*Spray Drying*, 1972, Master, Chapter 16.
*Current Medical Research and Opinion*, vol. 1, No. 10, 1973.
*Chemical Abstracts*, vol. 73, 1970, 54799t.

*Primary Examiner*—Frederick E. Waddell
*Attorney, Agent, or Firm*—Emmanuel J. Lobato; Robert E. Burns

[57] ABSTRACT

A process for producing an effective anti-ulcer preparation in the form of a dry powder by spray-drying a colloidal solution comprising bismuth citrate, ammonia and a polyhydric alcohol.

28 Claims, No Drawings

PHARMACEUTICAL COMPOSITIONS AND PROCESS FOR THEIR PREPARATION

This is a continuation of application Ser. No. 143,797, filed 4/25/80, which is a continuation of Ser. No. 726,195 filed 9/24/76, which is a continuation of Ser. No. 592,636 filed 7/2/75 which is a C-I-P of Ser. No. 543,862 filed 1/24/75 all of which have been abandoned.

The invention relates to new pharmaceutical compositions and to a process for their preparation.

The new pharmaceutical compositions according to the invention are bismuth-containing anti-ulcer preparations in solid form. Liquid compositions prepared from bismuth salts, such as bismuth citrate or bismuth subnitrate are known. Such liquid preparations have the disadvantage that they are less easy to store and to transport than solid compositions. They cannot easily be converted into an effective solid product, e.g. by simply heating and drying.

According to the invention an aqueous, colloidal solution comprising bismuth citrate, ammonia and a polyhydric alcohol is converted into a new pharmaceutical composition in the form of a dry power by spray-drying. The liquid starting material optionally contains pepsin, a colouring agent such as carmine, an alkali metal (e.g. sodium or potassium) hydroxide and a preservative, such as a mixture of soluble salts of esters of p-hydroxybenzoic acid, sold under the trade name Nipacombin A.

The known liquid preparations sometimes contain volatile liquids, such as ethanol and chloroform. Such liquids may be present in the starting material for the process of the invention in an amount not exceeding 15%, but they have virtually no effect on the process or on the product obtained. The three essential ingredients are used in preparing the solution. It is not certain, however, whether they are present as such in the liquid or that they form a new molecule or ion.

The quantities of the ingredients in the liquid may vary within wide limits. Liquids with a total amount of dissolved solids up to 40% (w/v) can effectively be spray-dried. Preferably 10–40 % and more particularly 11–16% of solids should be present.

The bismuth citrate content, calculated as $Bi_2O_3$, may at most be 10% (w/v), 2 to 6% being preferred.

The amount of ammonia used should at least be sufficient to keep the bismuth salt in solution. When expressed in proportion to the bismuth citrate (calculated as $Bi_2O_3$), the total amount of ammonia suitably ranges from 30 to 70% (w/w), preferably 50 to 60%.

A precipitate is formed when the pH of the liquid is too low or too high. The pH may range from 85 to 113. Preferably the pH is between 9 and 10.

The polyhydric alcohol may be chosen from disaccharides such as sucrose or maltose, monosaccharides such as fructose or glucose, hexitols, such as mannitol or sorbitol, and glycerol. The disaccharides, more particularly sucrose, and glycerol are preferred. The liquid may contain up to 25% (w/v) of polyhydric alcohol, preferably between 10 and 20%.

The dry powder according to the invention can be produced from the liquid in a conventional spray-drying unit. A suitable evaporative capacity is between 10 and 50 kgs $H_2O$ per hour, preferably between 10 and 25 kgs/h. The unit should preferably be provided with an air broom so that solid material adhering to the walls of the drying chamber can be removed continuously. Thus it is prevented that ingredients sensitive to heat (e.g. sucrose) are too long exposed to high temperatures. Generally, the heating time should be such that no undesired reaction takes place. For instance, when sucrose is used, the heating time should not exceed 20 minutes in order to prevent inversion.

The solution is preferably preheated at a temperature of 60° to 65° C. The solid product resulting from the process according to the invention is very hygroscopic. It is therefore recommended to remove the moisture from the spray-drying unit by preheating, for instance 30 minutes with an inlet temperature of about 200° C., and to carry out the drying with air of a low moisture content.

During the drying process the inlet temperature is preferably between 150° and 220° C., a temperature between 170° and 190° C. being particularly preferred, and the outlet temperature between 50° and 110° C., more particularly between 90° and 100° C. It will be understood that the speed at which the liquid is fed to the unit should be adapted to the evaporative capacity.

The solid products obtained by the described process are a feature of the invention. The powder can be administered orally as such or it may be dissolved in water to produce a palatable solution.

The invention also includes within its scope pharmaceutical compositions in dosage form for oral administration, such as capsules or tablets, containing the therapeutically active dry bismuth preparation as the active ingredient. The compositions may contain pharmaceutically-acceptable carriers.

The tablets may be formulated in the usual manner with one or more pharmaceutically-acceptable diluents or excipients, for example lactose or starch, and include materials of a lubricating nature, for example calcium stearate, or magnesium stearate. Capsules made of absorbable materials, such as gelatin, may contain the active substance alone or in admixture with a solid or liquid diluent.

The compositions according to the invention are therapeutically effective in the treatment of peptic ulcer, including gastric, duodenal and post-operative ulcer and peptic ulcer associated with hiatus hernia. Suitable daily dosages for adult humans correspond to 450–1000 mg of $Bi_2O_3$. The dosage for children will depend on their weight and age and may be calculated by methods commonly used in medical practice. The daily dose for children under 10 years will correspond to 150–400 mg of $Bi_2O_3$. The pharmaceutical compositions in dosage form therefore preferably have a bismuth content equivalent to 50–250 mg of $Bi_2O_3$.

The following Example illustrates the process of the invention.

EXAMPLE I 1,500 liter of liquid is prepared from
180.360 kg of bismuth citrate
118.279 l of ammonia 25%
7.125 kg of pepsin 1:10.000
23.700 kg of anhydrous citric acid
0.990 l of carmine nacarat
8.051 l of glycerol
330.000 kg of sucrose
39.900 kg of potassium hydroxide
3.000 kg of Nipacombin A 0.2%
8.700 l of chloroform
94.050 l of ethanol and purified water to produce the desired volumn.

The solution obtained is diluted with water to a solid-content of 12% and the diluted liquid is preheated at 60°-65° C. for 15 minutes. A spray-drying unit with an evaporative capacity of 10 kgs/h is preheated for 30 minutes with an inlet-air temperature of 200° C. The liquid is subsequently fed to the atomizer with a speed of 9 liters per hour, the inlet-air temperature being maintained at 180° C., and the dry power formed is collected.

The following Example illustrates a pharmaceutical composition according to the invention.

EXAMPLE II

Using known pharmaceutical techniques, tablets are prepared, containing 450 mg of the spray-dried product prepared according to Example I, 25 mg of Aerosil 200 (purified silicium dioxide),
    50 mg of corn starch
    5 mg of magnesium stearate.

The invention also includes within its scope the preparation of an aqueous solution from the dry powder. For instance, a solution suitable for oral administration may be obtained by dissolving 200 g of the powder prepared according to Example I in water to a volume of 1 liter. Other physiologically-acceptable substances may be added, for instance to produce a desired pH or to improve the taste of the solution.

We claim:

1. Process for the preparation of a new solid, bismuth-containing pharmaceutical composition from an aqueous colloidal liquid composition, comprising at most 40% (w/v) of dissolved solids, at most 10% (w/v) bismuth citrate calculated as $Bi_2O_3$, ammonia in an amount at least sufficient to keep the bismuth salt in colloidal solution and at most 25% of a polyhydric alcohol selected from the group consisting of disaccharides, monosaccharides, hexitols and glycerol, said colloidal liquid composition having a pH between 8.5 and 11.3, which comprises spray drying said colloidal liquid composition to obtain a dry therapeutical active powder, capable of combining with water to form a bismuth containing therapeutically active colloidal solution.

2. Process according to claim 1 in which the liquid starting material contains between 10 and 40% (w/v) of dissolved solids.

3. Process according to claim 1 in which the liquid starting material contains between 11 and 16% (w/v) of dissolved solids.

4. Process according to claim 1 in which the liquid starting material contains between 2 and 6% (w/v) of bismuth citrate, calculated as $Bi_2O_3$.

5. Process according to claim 1 in which the pH of the liquid starting material is between 9 and 10.

6. Process according to claim 1 in which the total amount of ammonia in the liquid starting material is between 30 and 70% (w/v) of the amount of bismuth citrate, calculated as $Bi_2O_3$.

7. Process according to claim 1 in which the total amount of ammonia in the liquid starting material is between 50 and 60% (w/w) of the amount of bismuth citrate, calculated as $Bi_2O_3$.

8. Process according to claim 1 in which the liquid starting material contains between 10 and 20% (w/v) of polyhydric alcohol.

9. Process according to claim 1 in which the polyhydric alcohol is selected from the group consisting of sucrose, maltose, fructose, glucose, mannitol, sorbitol and glycerol.

10. Process according to claim 9 in which the polyhydric alcohol is sucrose, maltose or glycerol.

11. Process according to claim 1 in which a spray-drying unit is used with an evaporative capacity between 10 and 50 kgs $H_2O$ per hour.

12. Process according to claim 11 in which a spray-drying unit is used with an evaporative capacity between 10 and 25 kgs $H_2O$ per hour.

13. Process according to claim 11 in which a spray-drying unit provided with an air broom is used.

14. Process according to claim 1 in which the liquid starting material is preheated at 60° to 65° C.

15. Process according to claim 1 in which the spray-drying unit is preheated and the drying is carried out with air of a low moisture content.

16. Process according to claim 15 in which the spray-drying unit is preheated at 200° C.

17. Process according to claim 1 in which the inlet air temperature is between 150° and 220° C.

18. Process according to claim 17 in which the inlet air temperature is between 170° and 190° C.

19. Process according to claim 1 in which the outlet air temperature is between 50° and 110° C.

20. A process according to claim 19 in which the outlet air temperature is between 90° and 100° C.

21. A dry powder obtained by the process of claim 1.

22. Pharmaceutical composition in dosage form for oral administration, comprising a therapeutically effective amount of a dry powder according to claim 21.

23. The pharmaceutical composition according to claim 22 having a bismuth content equivalent to 50–250 mg of $Bi_2O_3$.

24. Process for the preparation of a therapeutically effective liquid for oral administration, which comprises combining a therapeutically effective amount of the dry powder defined in claim 21 in water to obtain a colloidal solution.

25. The process of claim 1 in which the liquid starting composition contains about 10 to 40% (w/v) of dissolved solids, 2 to 6% (w/v) of bismuth citrate, calculated as $Bi_2O_3$, and ammonia in an amount of about 30 to 70% (w/w) of the amount of bismuth citrate, calculated as $Bi_2O_3$ and wherein said polyhydric alcohol is selected from the group consisting of sucrose, maltose, fructose, glucose, mannitol, sorbitol and glycerol.

26. A process according to claim 25 in which said polyhydric alcohol is present in an amount of about 10 to 20% (w/v).

27. The dry therapeutically active bismuth-containing powder capable of redissolving in water to form a bismuth containing therapeutically active colloidal solution, obtained by spray-drying an aqueous colloidal liquid; comprising between 10 to 40% (w/v) of dissolved solids, between 2 and 6% (w/v) bismuth citrate calculated as $Bi_2O_3$, ammonia in an amount of between 30 and 70% (w/v) of the amount of bismuth citrate calculated as $Bi_2O_3$, the amount of ammonia being at least sufficient to keep the bismuth salt in colloidal solution and up to 25% (w/v) of a polyhydric alcohol which is selected from the group consisting of sucrose, maltose, fructose, glucose, mannitol, sorbitol and glycerol, said liquid having a pH between about 9 and 10.

28. A dry therapeutically active bismuth-containing powder according to claim 27 in which said polyhydric alcohol is present in said colloidal liquid in an amount of about 10 to 20% (w/v).

* * * * *